US00PP25045P3

(12) United States Plant Patent
Hamilton et al.

(10) Patent No.: US PP25,045 P3
(45) Date of Patent: Nov. 11, 2014

(54) RASPBERRY PLANT NAMED 'DRISRASPSEVEN'

(50) Latin Name: ***Rubus idaeus* L.**
Varietal Denomination: DrisRaspSeven

(75) Inventors: Brian K. Hamilton, Richmond, TX (US); Carlos D. Fear, West Malling (GB); Matthias Vitten, Aptos, CA (US); Lluvia V. Gutierrez, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 218 days.

(21) Appl. No.: 13/507,923

(22) Filed: Aug. 7, 2012

(65) Prior Publication Data

US 2014/0047595 P1 Feb. 13, 2014

(51) Int. Cl.
*A01H 5/00* (2006.01)

(52) U.S. Cl.
USPC ..... Plt./204

(58) Field of Classification Search
CPC ..... A01H 5/0887; A01H 5/08; A01H 5/00; A01H 5/0216
USPC ..... Plt./204
See application file for complete search history.

*Primary Examiner* — June Hwu
(74) *Attorney, Agent, or Firm* — Jondle Plant Sciences Division of Swanson & Bratschun, L.L.C.

(57) ABSTRACT

A new and distinct variety of raspberry plant named 'DrisRaspSeven' particularly distinguished by having a self-fruitful plant that bears large, bright red berries, is disclosed.

2 Drawing Sheets

Genus and species: *Rubus idaeus* L.
Variety denomination: 'DrisRaspSeven'.

BACKGROUND OF THE NEW PLANT

The present invention relates to a new and distinct raspberry variety designated 'DrisRaspSeven' and botanically known as *Rubus idaeus* L. This new raspberry variety was discovered in Santa Cruz, Calif. in August 2005 and originated from a cross between the proprietary female parent raspberry plant 'Driscoll Cardinal' (U.S. Plant Pat. No. 14,903) and the proprietary male parent raspberry plant 'Driscoll Maravilla' (U.S. Plant Pat. No. 14,804). The original seedling of the new variety was first asexually propagated at a nursery in Santa Cruz, Calif. 'DrisRaspSeven' was subsequently asexually propagated and underwent further testing at a nursery in Santa Cruz, Calif. for seven years. The present invention has been found to be stable and reproduce true to type through successive asexual propagations via tissue culture and root cuttings.

Plant Breeder's Rights for this variety have not been applied for. 'DrisRaspSeven' has not been made publicly available or sold more than one year prior to the filing date of this application.

SUMMARY OF THE INVENTION

The following are the most outstanding and distinguishing characteristics of this new variety when grown under normal horticultural practices in Santa Cruz, Calif.:

1. Self-fruitful plant; and
2. Large, bright red berries.

DESCRIPTION OF THE PHOTOGRAPHS

This new raspberry plant is illustrated by the accompanying photographs which show fruit of the plant as well as the primocanes. The colors shown are as true as can be reasonably obtained by conventional photographic procedures. The photographs are of plants that are six months old.

DESCRIPTION OF THE NEW VARIETY

Figure 1:
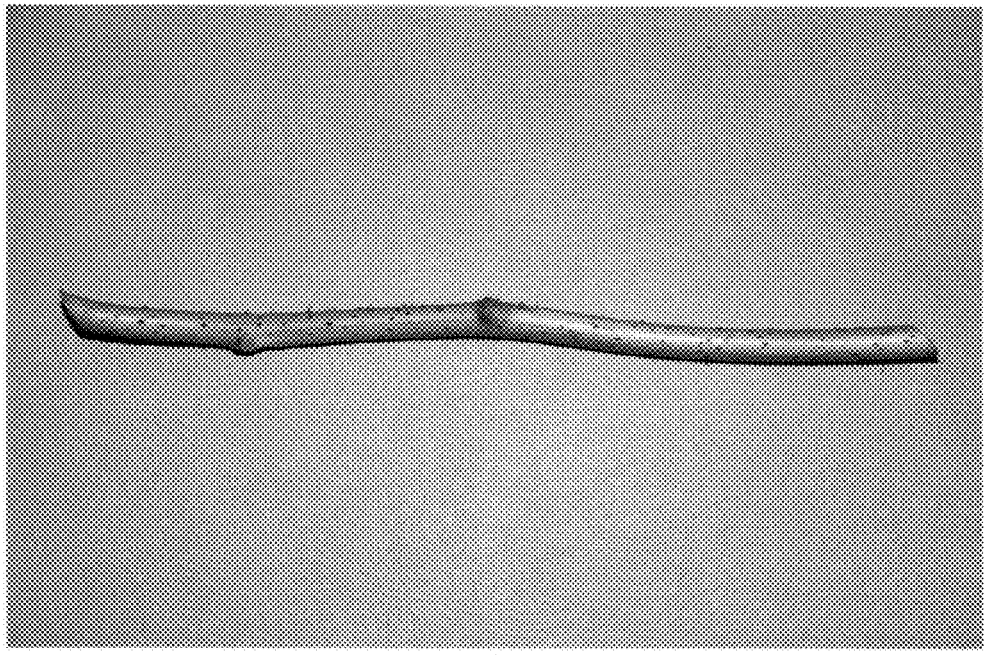
FIG. 1 shows a section of a young cane with prickles.
Figure 2:
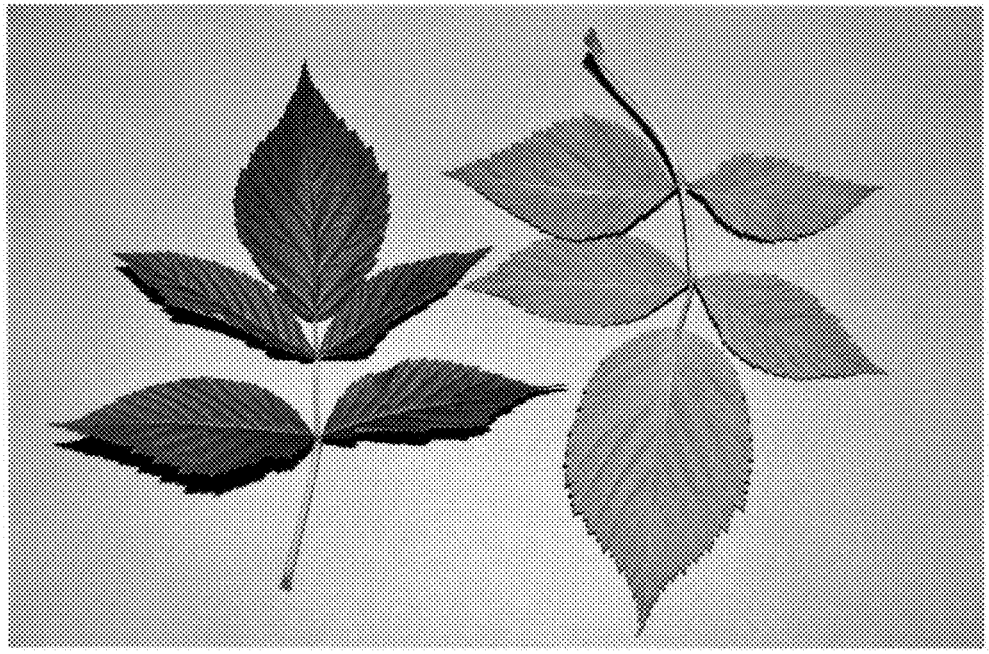
FIG. 2 shows both the upper surface and the lower surface of the plant leaves.
Figure 3:
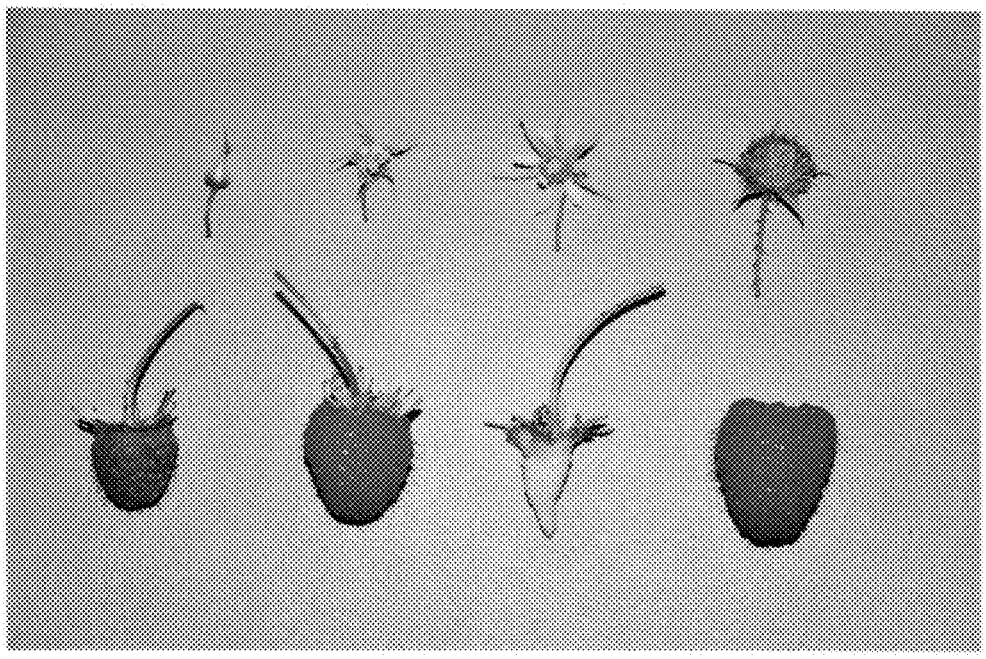
FIG. 3 shows close-up views of typical flowers and fruit at various stages of development.

The following detailed descriptions set forth the distinctive characteristics of 'DrisRaspSeven'. The data which define these characteristics is based on observations taken in Santa Cruz, Calif. from 2005 to 2011. This description is in accordance with UPOV terminology. Color designations, color descriptions, and other phenotypical descriptions may deviate from the stated values and descriptions depending upon variation in environmental, seasonal, climatic and cultural conditions. 'DrisRaspSeven' has not been observed under all possible environmental conditions. The botanical description of 'DrisRaspSeven' was taken from six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION

Classification:

*Family.*—Rosaceae.
*Botanical.*—*Rubus idaeus* L.
*Common name.*—Raspberry.
*Variety name.*—'DrisRaspSeven'.

Parentage:

*Female parent*.—The proprietary raspberry plant 'Driscoll Cardinal' (U.S. Plant Pat. No. 14,903).

*Male parent*.—The proprietary raspberry plant 'Driscoll Maravilla' (U.S. Plant Pat. No. 14,804).

Plant:

*Propagation*.—Tissue culture and root cuttings.

*Size*.—Medium.

*Height*.—18.5 cm.

*Width*.—14.6 cm.

*Length/width ratio*.—1.3.

*Productivity*.—Medium.

*Self-fruitfulness*.—Self-fruitful.

*New cane growth habit*.—Semi-erect.

Primocanes:

*Number of canes*.—Few; 7.

*Glaucosity (waxy bloom) on full grown shoot after picking*.—Medium.

*Cane length in autumn*.—Long.

*Cane length for current season's cane in autumn*.—19.4 cm.

*Length of internode*.—Medium.

*Internodal distance at central ⅓ of cane*.—5.8 cm.

*Length of vegetative bud*.—Medium.

*Number of young shoots*.—Medium; 9.

*Primocane color*.—RHS 144A.

*Anthocyanin coloration of apex during rapid growth*.—Absent.

*Intensity of anthocyanin coloration of apex during rapid growth*.—Absent.

*Time of young shoot emergence from the soil*.—Medium; last week of January.

*Time of beginning of flowers*.—Early; 2$^{nd}$ week of March.

*Time of beginning of fruit ripening in autumn*.—Medium; 3$^{rd}$ week of May.

*Length of fruiting period in autumn*.—Medium; 3$^{rd}$ week of May through 3$^{rd}$ week of September.

*Percent of cane flowering as primocane*.—35%.

*Percent primocane yield of total yield*.—60%.

*Glaucosity (waxy bloom) on current years cane in autumn*.—Medium.

*Cane strength*.—Medium.

*Shape of cane cross section*.—Rounded to angular.

*Pubescence on canes*.—Present.

Floricanes:

*Dormant cane length in summer*.—Medium (Pruned).

*Dormant cane color in summer*.—RHS 164A (Dark greyed-orange).

*Fruiting lateral attitude*.—Erect.

*Time of vegetative bud burst*.—Medium; 1$^{st}$ week of February.

*Time of beginning of flowers*.—Early; 1$^{st}$ week of April.

*Time of beginning of fruit ripening*.—Early; 1$^{st}$ week of May.

*Length of fruiting period*.—Medium.

Prickles (spines):

*Density of spines on central third*.—Medium.

*Size of base of prickles*.—Small.

*Length (from base to tip)*.—Short.

*Length at 1.0 m height at end of harvest season (from base to tip)*.—2.1 mm.

*Color (pigmentation)*.—RHS 166B (Dark greyed-orange).

*Attitude of tip*.—Horizontal to downward.

*Size*.—Small.

*Texture*.—Soft.

*Presence and distribution on petioles*.—Present and irregularly distributed.

Leaves:

*Terminal leaflet*.—Length: Long; 11.87 cm. Width: Medium; 7.12 cm. Length/width ratio: 1.7. Leaf color: Upper surface: RHS 137A (Dark green). Lower surface: RHS N138C (Medium green). Profile in cross section: Flat (straight). Relief between the veins: Medium. Overlapping of leaflets: Free. Glossiness: Medium. Shape: Ovate. Apex: Truncate. Base: Obtuse. Margin: Crenate. Arrangement: Simple.

*Lateral leaflets (basal pair)*.—Number of leaflets: Usually 5. Size: Length: 9.75 cm. Width: 5.37 cm. Length/width ratio: 1.8. Arrangement: Compound-opposite (2 leaves per node). Shape: Ovate. Apex: Truncate. Base: Cuneate. Margin: Doubly serrate. Lateral leaflet (length to stalklet, lower pair): Short.

*Rachis length between terminal leaflet and adjacent lateral leaflets*.—19.9 mm.

*Petiole*.—Size: Length: 1.1 mm. Diameter: 1.09 mm. Pigmentation: Upper surface: RHS 144A (Medium yellow-green). Lower surface: RHS 144C (Light yellow-green).

Stipules:

*Orientation*.—Erect.

Flowers:

*Size*.—Medium.

*Diameter*.—17.25 mm.

*Petal length*.—8.74 mm.

*Petal width*.—2.95 mm.

*Length/width ratio*.—3.0.

*Petal color*.—RHS 137D.

*Flower bud*.—Color: RHS 143C. Length: 15.79 mm. Width: 8.08 mm.

*Flowering period*.—Primocane: Medium; Early June to mid-September. Floricane: Medium; Late March to late June.

*Pedicel*.—Number of spines: Absent or very few. Color: RHS 144C. Anthocyanin coloration: Absent. Length: Very short; 13.44 mm. Diameter: 0.68 mm.

*Sepal*.—Color: RHS 143C. Length: 15.97 mm. Width: 5.56 mm.

Peduncle:

*Presence of anthocyanin coloration*.—Absent.

*Intensity of anthocyanin coloration*.—Absent or very weak.

*Color*.—RHS 144D.

Fruit:

*Length*.—Medium; 23.70 mm.

*Width*.—Medium; 21.32 mm.

*Ratio of length to width*.—1.1, as long as broad.

*Average number of drupelets per fruit*.—72.

*Weight (g/fruit)*.—Primocane: 6.1. Floricane: 5.8.

*Soluble solids (% in brix)*.—9.81.

*Weight of seeds (g/seed)*.—0.001503.

*Size*.—Large.

*Shape*.—Long conical.

*Size of single drupelet*.—Medium.

*Color*.—Immature fruit: RHS 145A (Medium yellow-green). Maturing fruit: RHS 58A (Medium red-purple). Mature fruit color: RHS 46A (Dark red).

*Glossiness*.—Medium.

*Firmness*.—Medium.

*Adherence to plug*.—Easy.

*Main bearing type*.—Both on previous years cane in summer and on current years cane in autumn.

*Time of ripening*.—Primocane: Medium; 1st week of July. Floricane: Medium; 1st week of April.

*Harvest season*.—Primocane: Mid-July to early October. Floricane: Mid-May to late July.

*Yield*.—High.

Pest and disease resistance: Not tested.

COMPARISON WITH PARENTAL AND COMMERCIAL VARIETIES

'DrisRaspSeven' differs from the proprietary female parent 'Driscoll Cardinal' (U.S. Plant Pat. No. 14,903) in that 'DrisRaspSeven' has a medium number of young shoots, medium glaucosity on primocanes, and leaves with medium relief between the veins, whereas 'Driscoll Cardinal' has many young shoots, weak glaucosity on primocanes, and leaves with weak relief between the veins. Additionally, 'DrisRaspSeven' has large fruit with an easy adherence to the plug, whereas 'Driscoll Cardinal' has medium sized fruit with medium adherence to the plug.

'DrisRaspSeven' differs from the proprietary male parent 'Driscoll Maravilla' (U.S. Plant Pat. No. 14,804) in that 'DrisRaspSeven' has terminal leaflets with an obtuse base and a crenate margin, whereas 'Driscoll Maravilla' has terminal leaflets with a round to cordate base and a doubly serrate margin. Additionally, 'DrisRaspSeven' has long conical shaped fruit with medium firmness, whereas 'Driscoll Maravilla' has ovate shaped fruit that is firm.

'DrisRaspSeven' differs from commercial variety 'DrisRaspThree' (U.S. Plant Pat. No. 23,477) in that 'DrisRaspSeven' has a medium sized plant having a semi-erect new cane growth habit, whereas 'DrisRaspThree' has a large sized plant having an erect or upright new cane growth habit. In addition, 'DrisRaspSeven' has large sized fruit with medium sized druplets, whereas 'DrisRaspThree' has medium to large sized fruit with large sized druplets.

We claim:

1. A new and distinct variety of raspberry plant named 'DrisRaspSeven' as described and shown herein.

* * * * *